(12) United States Patent
Buchanan et al.

(10) Patent No.: US 8,487,140 B2
(45) Date of Patent: Jul. 16, 2013

(54) PROCESS FOR PRODUCING PHENOL

(75) Inventors: John S. Buchanan, Lambertville, NJ (US); Jon E. Stanat, Westhampton Beach, NY (US); Tan-Jen Chen, Kingwood, TX (US); Jihad M. Dakka, Whitehouse Station, NJ (US); James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 322 days.

(21) Appl. No.: 12/996,219

(22) PCT Filed: Jul. 14, 2009

(86) PCT No.: PCT/US2009/050497
§ 371 (c)(1),
(2), (4) Date: Jan. 20, 2011

(87) PCT Pub. No.: WO2010/024975
PCT Pub. Date: Mar. 4, 2010

(65) Prior Publication Data
US 2011/0105805 A1      May 5, 2011

Related U.S. Application Data

(60) Provisional application No. 61/093,042, filed on Aug. 29, 2008.

(30) Foreign Application Priority Data

Nov. 18, 2008  (EP) .................................... 08169307

(51) Int. Cl.
*C07C 37/07*  (2006.01)
*C07C 37/08*  (2006.01)

(52) U.S. Cl.
USPC ........................................ 568/799; 568/798

(58) Field of Classification Search
None
See application file for complete search history.

(56) References Cited

U.S. PATENT DOCUMENTS

| | | | |
|---|---|---|---|
| 2,291,585 A | 7/1942 | Bartlett et al. |
| 3,076,810 A | 2/1963 | Duggan et al. |
| 3,194,843 A | 7/1965 | Silber et al. |
| 3,211,668 A | 10/1965 | Yamamoto |
| 3,238,120 A | 3/1966 | Sale |
| 3,247,278 A | 4/1966 | Garwood et al. |
| 3,358,044 A | 12/1967 | Russell et al. |
| 3,442,958 A | 5/1969 | Choo |
| 3,514,492 A | 5/1970 | Juguin et al. |
| 3,519,575 A | 7/1970 | Bozik et al. |
| 3,534,110 A | 10/1970 | Juguin et al. |
| 3,534,116 A | 10/1970 | Fuller |
| 3,580,970 A | 5/1971 | Swift |
| 3,691,102 A | 9/1972 | Swift |
| 3,775,487 A | 11/1973 | Isbitsky, Jr. et al. |
| 4,021,490 A * | 5/1977 | Hudson ........................ 568/342 |
| 4,088,603 A | 5/1978 | Carter et al. |
| 4,162,267 A | 7/1979 | Fisher et al. |
| 4,167,456 A | 9/1979 | Murtha |
| 4,169,857 A | 10/1979 | Murtha |
| 4,258,268 A | 3/1981 | Björnson |
| 4,328,372 A | 5/1982 | Wu |
| 4,417,076 A | 11/1983 | Rozovsky et al. |
| 4,434,299 A | 2/1984 | Chang et al. |
| 4,520,129 A | 5/1985 | Murtha |
| 4,929,762 A | 5/1990 | Matsunaga et al. |
| 4,933,507 A | 6/1990 | Inoki et al. |
| 4,999,326 A | 3/1991 | Sikkenga et al. |
| 5,057,296 A | 10/1991 | Beck |
| 5,087,792 A | 2/1992 | Cottrell et al. |
| 5,102,643 A | 4/1992 | Kresge et al. |
| 5,180,871 A | 1/1993 | Matsunaga et al. |
| 5,256,348 A | 10/1993 | Waller |
| 5,292,960 A | 3/1994 | Meier et al. |
| 5,310,713 A | 5/1994 | Kojima et al. |
| 5,319,148 A | 6/1994 | Karcher et al. |
| 5,395,976 A | 3/1995 | Scharschmidt et al. |
| 5,569,635 A | 10/1996 | Moy et al. |
| 6,037,513 A | 3/2000 | Chang et al. |
| 6,376,422 B1 | 4/2002 | McNabb et al. |
| 6,579,821 B1 | 6/2003 | Ginosar et al. |
| 6,916,756 B2 | 7/2005 | Schindler et al. |

(Continued)

FOREIGN PATENT DOCUMENTS

| | | |
|---|---|---|
| DE | 100 18 724 | 10/2001 |
| EP | 0 319 302 | 6/1989 |

(Continued)

OTHER PUBLICATIONS

R.B. Borade et al., "*Selective dehydrogenation of cyclohexene to benzene using Pd-exchanged α-zirconium phosphate*", Catalysis Letters, vol. 45, pp. 233-235, 1997.

(Continued)

*Primary Examiner* — Brian J Davis

(74) *Attorney, Agent, or Firm* — Anthony G. Boone; Jamie L. Sullivan; Siwen Chen

(57) ABSTRACT

In a process for producing phenol, cyclohexylbenzene is oxidized to produce cyclohexylbenzene hydroperoxide and then the resultant cyclohexylbenzene hydroperoxide is cleaved to produce an effluent stream comprising phenol and cyclohexanone. At least a portion of the effluent stream is then fed to at least one dehydrogenation reaction zone, where the effluent stream portion is contacted with a dehydrogenation catalyst under conditions effective to convert at least part of the cyclohexanone in the effluent portion into phenol and hydrogen.

16 Claims, 1 Drawing Sheet

U.S. PATENT DOCUMENTS

| | | | |
|---|---|---|---|
| 7,115,538 | B2 | 10/2006 | Buchanan et al. |
| 7,256,149 | B2 | 8/2007 | Grey et al. |
| 7,285,512 | B2 | 10/2007 | Bai et al. |
| 7,285,685 | B2 | 10/2007 | Walsdorff et al. |
| 7,396,798 | B2 | 7/2008 | Ma et al. |
| 7,538,066 | B2 | 5/2009 | Soled et al. |
| 2007/0032681 | A1 | 2/2007 | Walsdorff et al. |
| 2008/0039315 | A1 | 2/2008 | Ma et al. |
| 2009/0215612 | A1 | 8/2009 | McCarthy et al. |

FOREIGN PATENT DOCUMENTS

| | | |
|---|---|---|
| EP | 1 050 339 | 11/2000 |
| EP | 1 288 188 | 3/2003 |
| EP | 1 430 949 | 6/2004 |
| FR | 1509921 | 1/1968 |
| FR | 1541720 | 10/1968 |
| GB | 986931 | 3/1965 |
| GB | 1013715 | 12/1965 |
| JP | 06-263668 | 9/1994 |
| JP | 07-188082 | 7/1995 |
| JP | 2637812 | 8/1997 |
| JP | 2007/269522 | 10/2007 |
| WO | 00/67902 | 11/2000 |
| WO | 01/15803 | 3/2001 |
| WO | 01/74767 | 10/2001 |
| WO | 2007/009904 | 1/2007 |
| WO | 2008/066274 | 6/2008 |
| WO | 2008/128638 | 10/2008 |
| WO | 2009/131769 | 10/2009 |
| WO | 2009/134514 | 11/2009 |
| WO | 2010/024975 | 3/2010 |

OTHER PUBLICATIONS

A. Corma, "From Microporous to Mesoporous Molecular Sieve Materials and Their Use in Catalysis", Chem. Rev., vol. 97, pp. 2373-2419, 1997.

S. Kamiguchi et al., "Catalytic Hydrodehydration of Cyclohexanone, Hydrogenation of 2-Cyclohexen-1-one, and Dehydrogenation of Cyclohexene over a Mo Chloride Cluster with an Octahedral Metal Framework", Journal of Cluster Science, vol. 16, No. 1, pp. 77-91, 2005.

M. Lezanska et al., "Characterization of Cr-MCM-41 and Al, Cr-MCM-14 Mesoporous Catalyst for Gas-Phase Oxidative Dehydrogenation of Cyclohexane", J. Phys. Chem. C., vol. 111, pp. 1830-1839, 2007.

M. Masai et al., "Dehydrogenation Activity of Nickel-Tin-Silica Catalyst", Journal of Catalysis, vol. 38, pp. 128-134, 1975.

M.C. Samolada et al., "Catalyst Evaluation for Catalytic Biomass Pyrolysis", Energy & Fuels, vol. 14, pp. 1161-1167, 2000.

B. Solsona et al., "Vanadium Oxide Supported on Mesoporous MCM-41 as Selective Catalyst in the Oxidative Dehydrogenation of Alkanes", Journal of Catalysis, vol. 203, pp. 443-452, 2001.

W. Spieker et al., "Experimental Investigation and Modeling of Platinum Adsorption onto Ion-modified Silica and Alumina", Studies in Surface Science and Catalysis, vol. 130, pp. 203-208, 2000.

Cesar et al., "Stability and Selectivity of Bimetallic Cu-Co/$SiO_2$ Catalysts for Cyclohexanol Dehydrogenation", Applied Catalysis A: General, 1999, vol. 176, No. 2, pp. 205-212.

Chen et al., "Nonoxidative Dehydrogenation of Cyclohexanol over Copper-Iron Binary Oxides", Applied Catalysis A: General, 1992, vol. 83, No. 2, pp. 201-211.

Dobrovolszky et al., "Catalytic Transformations of Cyclohexanol on Group VIII Metal Catalysts", Journal of Catalysis, 1982, vol. 74, No. 1, pp. 31-43.

Fridman et al., "Dehydrogenation of Cyclohexanol on Copper-Containing Catalysts:I. The Influence of the Oxidation State of Copper on the Activity of Copper Sites", Journal of Catalysis, 2000, vol. 195, No. 1, pp. 20-30.

Masai et al., "Dehydrogenation and Hydrogenation Activity of Palladium-Tin-Silica and Nickel-Tin-Silica", Journal of Catalysis, 1977, vol. 50, No. 3, pp. 419-428.

Fridman et al., "Dehydrogenation of Cyclohexanol on Copper-Zinc Catalysts", Neftekhimiya, 1989, vol. 29, No. 1, pp. 48-51 (Abstract Only).

Nikiforova et al., "Dehydrogenation of Cyclohexanol on Copper Applied on Magnesia Oxide", Neftekhimiya, 1972, vol. 12, No. 4, pp. 475-480 (Abstract Only).

Paal et al., "Radiotracer Investigation of Transformations of Cyclohexanol in the Presence of a Nickel Powder Catalyst", Z Phys Chem, 1974, vol. 91, No. 1-4, pp. 54-66.

Arends, I., et al., "Selective Catalytic Oxidation of Cyclohexylbenzene to Cyclohexylbenzene-1-Hydroperoxide: A Coproduct-Free Route to Phenol" Tetrahedron, 2002, vol. 58, pp. 9055-9061.

Saito, Y., et al."Performance of activity test on supported Pd catalysts for dehydrogenation of cyclohexanone to phenol (effect of supports on activity)", Ibaraki Kogyo Koto Senmon Gakko Kenkyu Iho (1995), vol. 30, pp. 39-46—English Abstract Only.

Swift, H. et al., "Metallic Phases and Activites of Nickel-Tin-Silica Catalysts Dehydrogenation of Cyclohexanone, Cyclohexanol, and Cyclohexane", Journal of Catalysis, 1968, vol. 12, pp. 5-14.

Milczanowski, S., et al., "Catalytic Dehydrogenation of Cyclohexanone to Phenol", PrZEMYSL Cheniczny, 1978, vol. 57, No. 3, pp. 129-130—English Abstract Only.

Waligora, B., et al., Waligora, B., et al., "Catalytic Dehydrogenation of Mixture of Cyclohexanol and Cyclohexanon to Phenol", Prace Chemiczne, 1982, vol. 27, pp. 93-99—English Abstract Only.

\* cited by examiner

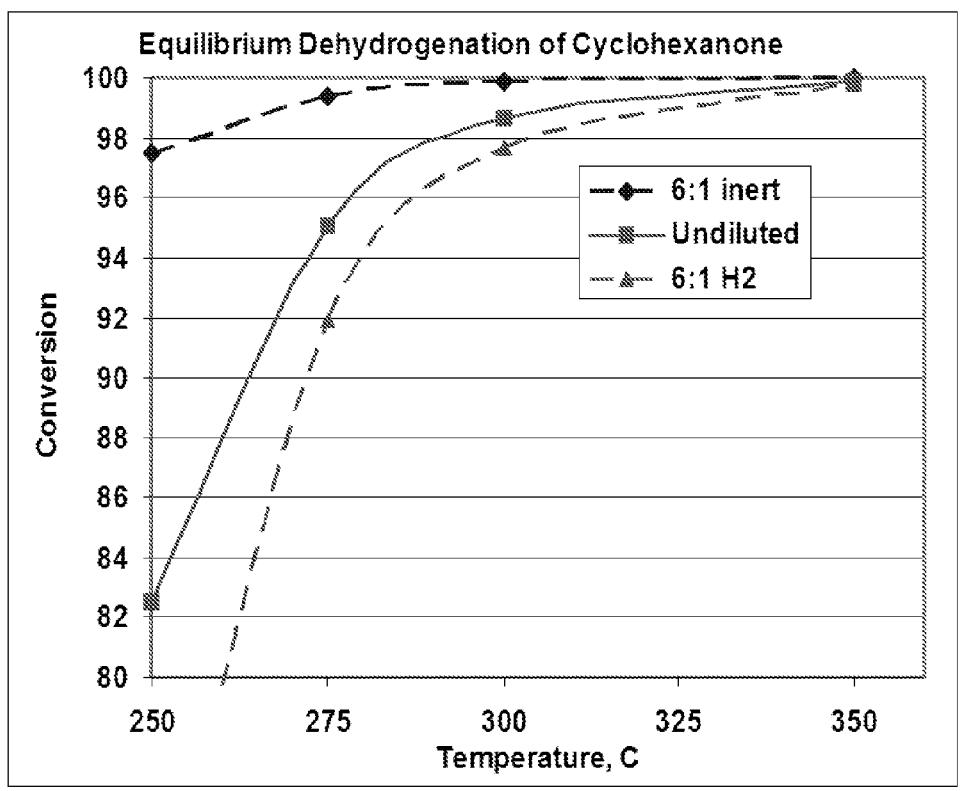

under hydroalkylation conditions to produce cyclohexylbenzene feed. In addition, although the cleavage effluent portion subjected to the dehydrogenation step can be a substantially pure cyclohexanone fraction produced by separation of the phenol and light and heavy ends from the raw effluent, given the cost of this separation, the process can also be applied to an effluent portion containing some or all of the phenol produced in the cleavage step. In this way, the total cost of purifying the final phenol stream and, if present, the final cyclohexanone stream can be minimized.

PROCESS FOR PRODUCING PHENOL

CROSS REFERENCE TO RELATED APPLICATION

This application is a National Stage Application of International Application No. PCT/US2009/050497 filed Jul. 14, 2009, which claims the benefit of prior U.S. provisional application Ser. No. 61/093,042 filed Aug. 29, 2008, and European Application No. 08169307.9 filed Nov. 18, 2008, all of which are hereby incorporated by reference in their entirety.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of cyclohexylbenzene (analogous to cumene oxidation) could offer an alternative route for phenol production without the problem of acetone co-production. This alternative route proceeds through cyclohexylbenzene hydroperoxide, which is cleaved to produce phenol and cyclohexanone in substantially equimolar amounts.

However, one problem in producing phenol by way of the cleavage of cyclohexylbenzene hydroperoxide is that the cyclohexanone and phenol produce an azeotropic mixture composed of 28 wt % cyclohexanone and 72 wt % phenol. Thus any attempt to separate the cleavage effluent by simple distillation results in this azeotropic mixture. Moreover, although cyclohexanone is a valuable product with a growing market, there is currently no large worldwide merchant market for cyclohexanone; most cyclohexanone is made as an intermediate and consumed on the spot. In some cases, therefore, it may be desirable to increase the amount of phenol in the product mix from the oxidation of cyclohexylbenzene or even produce all phenol with no cyclohexanone. According to the present invention, an integrated process for producing phenol from cyclohexylbenzene is provided that facilitates control of the amount of cyclohexanone in the final product.

In particular, the present invention provides a process for producing phenol by oxidation of cyclohexylbenzene to cyclohexylbenzene hydroperoxide followed by cleavage of the cyclohexylbenzene hydroperoxide, in which at least a portion of the effluent from the cleavage step is subjected to a dehydrogenation step. The dehydrogenation not only converts at least part of the cyclohexanone in the effluent portion to additional phenol but also generates hydrogen as a by-product, which can, for example, be recycled to an initial benzene hydroalkylation step for producing the cyclohexylbenzene feed. In addition, although the cleavage effluent portion subjected to the dehydrogenation step can be a substantially pure cyclohexanone fraction produced by separation of the phenol and light and heavy ends from the raw effluent, given the cost of this separation, the process can also be applied to an effluent portion containing some or all of the phenol produced in the cleavage step. In this way, the total cost of purifying the final phenol stream and, if present, the final cyclohexanone stream can be minimized.

SUMMARY

In one aspect, the invention resides in a process for producing phenol, the process comprising:

(a) oxidizing cyclohexylbenzene to produce cyclohexylbenzene hydroperoxide;

(b) converting cyclohexylbenzene hydroperoxide from (a) to produce an effluent stream comprising phenol and cyclohexanone;

(c) feeding at least a portion of said effluent stream to at least one dehydrogenation reaction zone; and (d) contacting said at least a portion of said effluent stream with a dehydrogenation catalyst in said dehydrogenation reaction zone under dehydrogenation conditions including a temperature of about 250° C. to about 500° C. effective to convert at least part of the cyclohexanone in said at least a portion of said effluent stream into phenol and hydrogen.

In one embodiment, said at least a portion of said effluent stream fed to said dehydrogenation reaction zone has the same composition as the effluent stream produced by said converting (b).

In another embodiment, the process further includes subjecting the effluent stream produced by said converting (b) to at least one separation step such that said at least a portion of said effluent stream fed to said dehydrogenation reaction zone contains less phenol than the effluent stream producing by said converting (b). Conveniently, the effluent stream produced by said converting (b) is subjected to at least one separation step such that said at least a portion of said effluent stream fed to said dehydrogenation reaction zone contains less than 50 wt %, for example less than 30 wt %, such as less than 1 wt %, phenol. In addition, the effluent stream produced by said converting (b) may be subjected to at least one separation step to remove components boiling below 155° C. (as measured at 101 kPa) and/or components boiling above 182° C. (as measured at 101 kPa), prior to feeding said at least a portion of said effluent stream to said dehydrogenation reaction zone.

Conveniently, said dehydrogenation conditions in (d) comprise a temperature of about 300° C. to about 450° C.

Conveniently, said conditions in (d) comprise a pressure of about 0.01 atm to about 20 atm (1 kPa to 2000 kPa), such as about 1 atm to about 3 atm (100 kPa to 300 kPa).

Conveniently, hydrogen is fed to said dehydrogenation reaction zone together with said at least a portion of said effluent stream, typically such that the molar ratio of hydrogen to cyclohexanone in the feed to the dehydrogenation reaction zone is about 0:1 to about 4:1. Conveniently, at least part of the hydrogen fed to said dehydrogenation reaction zone is hydrogen produced in said contacting (d).

In a further aspect, the invention resides in a process for producing phenol from benzene, the process comprising:

(a1) contacting benzene and hydrogen with a catalyst under hydroalkylation conditions to produce cyclohexylbenzene;

(a) oxidizing cyclohexylbenzene from (a1) to produce cyclohexylbenzene hydroperoxide;

(b) converting cyclohexylbenzene hydroperoxide from (a) to produce an effluent stream comprising phenol and cyclohexanone;

(c) feeding at least a portion of said effluent stream to at least one dehydrogenation reaction zone;

(d) contacting said at least a portion of said effluent stream with a dehydrogenation catalyst in said dehydrogenation reaction zone under dehydrogenation conditions effective to convert at least part of the cyclohexanone in said at least a portion of said effluent stream into phenol and hydrogen; and (e) recycling at least part of the hydrogen produced in said contacting (d) to said contacting (a1).

BRIEF DESCRIPTION OF THE DRAWINGS

FIG. 1 is a graph, based on thermodynamic calculations, of conversion against temperature for the dehydrogenation of cyclohexanone at atmospheric pressure (101 kPa) both with and without the addition of a nitrogen diluent and hydrogen.

DETAILED DESCRIPTION OF THE EMBODIMENTS

Described herein is a process for producing phenol that allows the co-produced cyclohexanone to be partially or totally converted to additional phenol. In the present process, cyclohexylbenzene, generally produced by the catalytic hydroalkylation of benzene, is oxidized to produce cyclohexylbenzene hydroperoxide and then the cyclohexylbenzene hydroperoxide is cleaved to produce an effluent stream comprising phenol and cyclohexanone in substantially equimolar amounts. At least a portion of the effluent is then fed to a dehydrogenation reaction zone, where the effluent stream portion is contacted with a dehydrogenation catalyst under dehydrogenation conditions effective to convert the cyclohexanone in said effluent portion into additional phenol and into hydrogen, which can be recycled to the benzene hydroalkylation step (when present).

Production of Cyclohexylbenzene

The cyclohexylbenzene employed in the present process can be produced by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

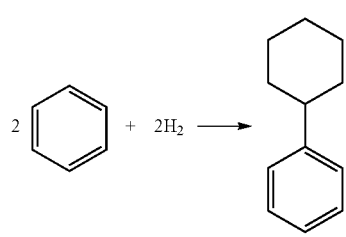

(1)

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. Conveniently, the total feed typically contains less than 100 ppm, such as less than 30 ppm, for example less than 3 ppm, sulfur. Conveniently the total feed typically contains less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C. Suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is preferably a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0 293 032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina and/or titania and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay and/or silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. and/or a pressure of about 800 to about 3500 kPa and/or a weight hourly space velocity of about 1 to about 10 $hr^{-1}$ on total feed and/or a benzene/dicyclohexylbenzene weight ratio about of 1:1 to about 5:1.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-trihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C. and/or a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C. and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

Post Treatment of Cleavage Effluent

The effluent from the cleavage reaction comprises phenol and cyclohexanone in substantially equimolar amounts. The present process provides an advantageous route to increasing the amount of phenol produced from the original CHB or benzene feed by contacting at least part of the cleavage effluent with a dehydrogenation catalyst so as to convert some or all of the cyclohexanone in the effluent into additional phenol according to the reaction (2):

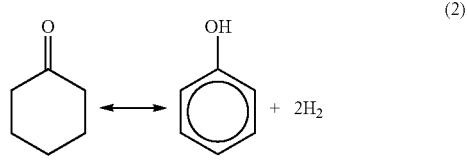

(2)

Any suitable dehydrogenation catalyst can be used in reaction (2), such as, for example, the promoted nickel catalysts described in U.S. Pat. No. 4,417,076. Suitable conditions for the dehydrogenation step comprise a temperature of about 250° C. to about 500° C. and/or a pressure of about 0.01 atm to about 20 atm (1 kPa to 2000 kPa), such as a temperature of about 300° C. to about 450° C. and a pressure of about 1 atm to about 3 atm (100 kPa to 300 kPa).

In the above temperature ranges, the dehydrogenation of cyclohexanone is equilibrium-limited. FIG. 1 is a graph showing the maximum extent of the dehydrogenation reaction, under the designated conditions, based on thermodynamic calculations made using free energy data in *The Chemical Thermodynamics of Organic Compounds*, by D. R. Stull, E. F. Westrum, and G. C. Sinke, published by Robert E. Krieger Publishing Company, Malabar, Fla. (1987). Standard thermodynamic calculations (see, e.g. *Chemical Engineering Thermodynamics*, R. E. Balzhiser, M. R. Samuels, and J. D. Eliassen; Prentice-Hall, Englewood Cliffs, N.J. (1972) were used to estimate the equilibrium conversion of cyclohexanone to phenol. FIG. 1 indicates that at 1 atmosphere (101 kPa) total pressure and with pure cyclohexanone feed, it is necessary to operate at or above 275° C. in order to achieve at least 90% conversion of cyclohexanone to phenol. Running at lower total pressure, or diluting with a gas inert to the reaction, such as nitrogen and/or methane, increases the equilibrium conversion, whereas cofeeding hydrogen tends to reduce equilibrium conversion. However, cofeeding hydrogen assists in extracting the hydrogen generated in the dehydrogenation reaction for use in other process steps, particularly for the (optional) benzene hydroalkylation step, and also frequently improves catalyst stability. Where hydrogen is cofed to the dehydrogenation reaction, the rate of hydrogen addition is typically such that the molar ratio of hydrogen to cyclohexanone in the feed to the dehydrogenation reaction is about 0:1 to about 4:1.

The reactor configuration used for the dehydrogenation process generally comprises one or more fixed bed reactors containing a solid catalyst with a dehydrogenation function. Per-pass conversion of cyclohexanone is typically greater than 70%, and preferably greater than 90%. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of 30 to 100° C. across each bed. Preferably the last bed in the series runs at a higher exit temperature than the first bed in the series.

As previously stated, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490, 4,019,965, 4,115,207, 4,115,204, 4,115,206, 4,201,632, 4,230,638, 4,167,456, 4,115,205, and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The separation of phenol is conveniently effected by vacuum and/or extractive distillation. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can be readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including for example a temperature of about 20° C. to about 250° C. and/or a pressure of about 101 kPa to about 10000 kPa and/or a hydrogen to phenol molar ratio of about 1:1 to about 100:1.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) oxidizing cyclohexylbenzene to produce cyclohexylbenzene hydroperoxide;
   (b) converting cyclohexylbenzene hydroperoxide from (a) to produce an effluent stream comprising phenol and cyclohexanone;
   (c) feeding at least a portion of said effluent stream to at least one dehydrogenation reaction zone; and
   (d) contacting said at least a portion of said effluent stream with a dehydrogenation catalyst in said dehydrogenation reaction zone under dehydrogenation conditions including a temperature of 250° C. to 500° C. effective to convert at least part of the cyclohexanone in said at least a portion of said effluent stream into phenol and hydrogen.

2. A process for producing phenol from benzene, the process comprising:
   (a1) contacting benzene and hydrogen with a catalyst under hydroalkylation conditions to produce cyclohexylbenzene;
   (a) oxidizing cyclohexylbenzene from said contacting (a1) to produce cyclohexylbenzene hydroperoxide;
   (b) converting cyclohexylbenzene hydroperoxide from said oxidizing (a) to produce an effluent stream comprising phenol and cyclohexanone;
   (c) feeding at least a portion of said effluent stream to at least one dehydrogenation reaction zone;
   (d) contacting said at least a portion of said effluent stream with a dehydrogenation catalyst in said dehydrogenation reaction zone under dehydrogenation conditions effective to convert at least part of the cyclohexanone in said at least a portion of said effluent into phenol and hydrogen; and
   (e) recycling at least part of the hydrogen produced in (d) to said contacting (a1).

3. The process of claim 2, wherein said dehydrogenation conditions include a temperature of 250° C. to 500° C.

4. The process of claim 1, wherein said at least a portion of said effluent stream fed to said dehydrogenation reaction zone has the same composition as the effluent stream produced by said converting (b).

5. The process of claim 1, and further including subjecting the effluent stream produced by said converting (b) to at least one separation step such that said at least a portion of said effluent stream fed to said dehydrogenation reaction zone contains less phenol than the effluent stream produced by said converting (b).

6. The process of claim 5, and further including subjecting the effluent stream produced by said converting (b) to at least one separation step such that said at least a portion of said effluent stream fed to said dehydrogenation reaction zone contains less than 50 wt % phenol.

7. The process of claim 1, and further including subjecting the effluent stream produced by said converting (b) to at least one separation step to remove components boiling below 155° C. (as measured at 101 kPa) prior to feeding said at least a portion of said effluent stream to said dehydrogenation reaction zone.

8. The process of claim 1, and further including subjecting the effluent stream produced by said converting (b) to at least one separation step to remove components boiling above 182° C. (as measured at 101 kPa) prior to feeding said at least a portion of said effluent stream to said dehydrogenation reaction zone.

9. The process of claim 1, wherein said dehydrogenation conditions comprise a temperature of 300° C. to 450° C.

10. The process of claim 1, wherein said dehydrogenation conditions comprise a pressure of 1 kPa to 2000 kPa (0.01 atm to 20 atm).

11. The process of claim 10, wherein the pressure is from 100 kPa to 300 kPa (1 atm to 3 atm).

12. The process of claim 1, wherein in said feeding (c), hydrogen is fed to said dehydrogenation reaction zone together with said at least a portion of said effluent stream.

13. The process of claim 12, wherein at least part of the hydrogen fed to said dehydrogenation reaction zone in said feeding (c) is hydrogen produced in said contacting (d).

14. The process of claim 12, wherein the molar ratio of hydrogen to cyclohexanone in the feed to the dehydrogenation reaction zone is 0:1 to 4:1.

15. The process of claim 1, wherein said at least a portion of said effluent stream is fed to a plurality of dehydrogenation reaction zones connected in series.

16. The process of claim 5, further including subjecting the effluent stream produced by said converting (b) to at least one separation step such that said at least a portion of said effluent stream fed to said dehydrogenation reaction zone contains less than 1 wt % phenol.

* * * * *